(12) United States Patent
Kieffer et al.

(10) Patent No.: US 8,174,557 B2
(45) Date of Patent: May 8, 2012

(54) DEPLOYABLE SENSOR DEVICE, SENSOR SYSTEM, AND METHOD OF COLLECTING ENVIRONMENTAL INFORMATION

(75) Inventors: Kevin Kieffer, Washington, DC (US); James Wiggins, Thurmont, MD (US); Barclay Roman, Clifton, VA (US); Peter Owen, Monrovia, MD (US); Conrad Zeglin, Rockville, MD (US); Todd Stawarz, Fairfax, VA (US)

(73) Assignee: Adaptive Methods, Inc., Rockville, MD (US)

( * ) Notice: Subject to any disclaimer, the term of this patent is extended or adjusted under 35 U.S.C. 154(b) by 719 days.

(21) Appl. No.: 12/326,225

(22) Filed: Dec. 2, 2008

(65) Prior Publication Data

US 2010/0134604 A1 Jun. 3, 2010

(51) Int. Cl.
*H04N 7/14* (2006.01)
(52) U.S. Cl. .................. 348/14.05; 348/373; 340/853.2
(58) Field of Classification Search ............... 348/14.05, 348/73, 373; 340/853.2
See application file for complete search history.

(56) References Cited

U.S. PATENT DOCUMENTS

| 4,668,940 | A  | * | 5/1987  | Beard et al. ............... 340/521 |
| 4,709,265 | A  | * | 11/1987 | Silverman et al. .......... 348/158 |
| 7,014,502 | B2 | * | 3/2006  | Rasmussen ................ 439/578 |
| 7,333,148 | B2 | * | 2/2008  | Chang et al. ............... 348/374 |
| 7,733,416 | B2 | * | 6/2010  | Gal .......................... 348/373 |
| 2008/0062258 | A1 | * | 3/2008 | Bentkovski et al. ......... 348/50 |
| 2010/0179691 | A1 | * | 7/2010 | Gal et al. .................. 700/259 |

* cited by examiner

*Primary Examiner* — Viet Vu
(74) *Attorney, Agent, or Firm* — Dickstein Shapiro LLP

(57) ABSTRACT

A system for obtaining and displaying such images and environmental information from environments is disclosed, as well as a sensor device and a host configured for use in the system, the sensor device having camera assemblies, environmental sensors, and being connected to the host via a wireless communications link. Methods for obtaining and presenting the images and environmental information using system 100 are also disclosed.

45 Claims, 8 Drawing Sheets

DEPLOYABLE SENSOR DEVICE, SENSOR SYSTEM, AND METHOD OF COLLECTING ENVIRONMENTAL INFORMATION

STATEMENT REGARDING FEDERALLY SPONSORED RESEARCH OR DEVELOPMENT

Pursuant to 35 U.S.C. §202(c)(6) of the Patent Act, Applicants specify that this invention was made, in part, with U.S. government support under Department of Defense (DOD) grant number N65538-08-M-0016. The government may have certain rights in the invention.

FIELD OF THE INVENTION

The invention relates to the detection and collection of information and images in an environment, and in particular to systems, methods, and apparatus for collecting the information and images.

BACKGROUND

Collection of images and detection of environmental conditions, particularly in a hazardous environment, is critical to rapid situational assessment and damage control. For example, damage sustained on board a boat or other naval vessel, whether due to enemy attack or accident, presents a situation which may require rapid situational assessment and damage control in a potentially hazardous environment. Rapid situational assessment of environments such as the compartment of a ship, including views within the compartment and detection of heat and/or other potentially hazardous environmental conditions, is essential for coordinating a response and mitigating damage to rescuers, responders, victims, and property.

During an event including a hazardous environment, responders may need to inspect rooms, areas, or other compartments that may have been exposed to dangerous and possibly lethal environmental conditions. Even if the hazardous environmental conditions were known, response may be slowed due to the need for responders to don protective gear and physically avoid hazards. In some situations, it may be impossible for a human to assess an area due to fire, flooding, or other environmental conditions for which there is no protection.

Accordingly, there is a need and desire for a system and method for assessing environmental conditions and obtaining images from potentially hazardous environments, while preserving the health and lives of the damage control teams.

DETAILED DESCRIPTION OF THE INVENTION

Figure 1:
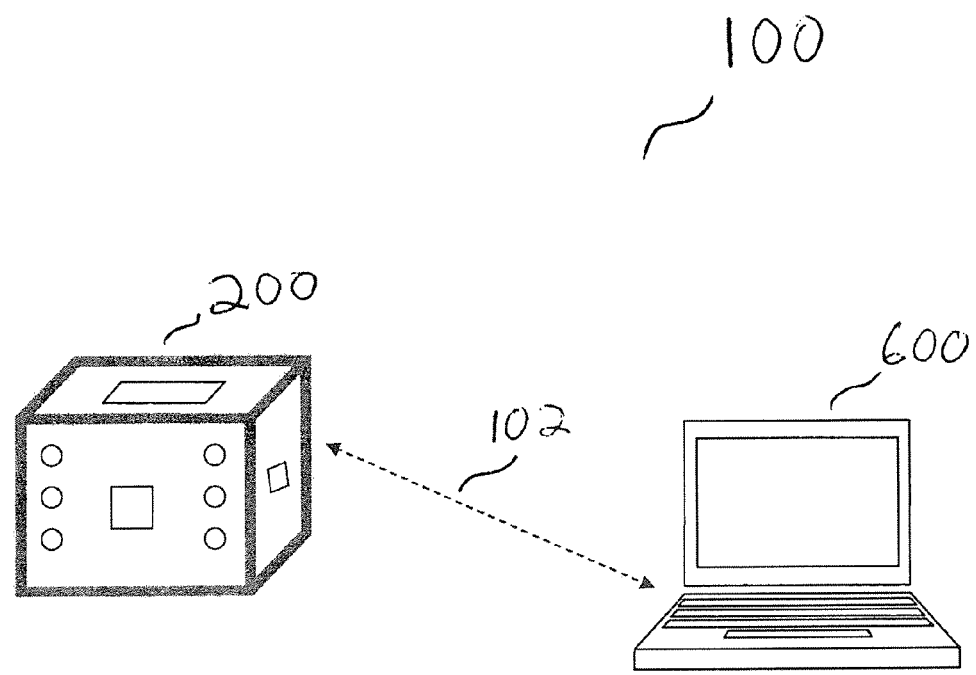
FIG. 1 is a diagram of a system for obtaining environmental information and images, in accordance with embodiments described herein.

In the following detailed description, reference is made to the accompanying drawings, which form a part hereof and illustrate specific embodiments that may be practiced. In the drawings, like reference numerals describe substantially similar components throughout the several views. These embodiments are described in sufficient detail to enable those skilled in the art to practice them, and it is to be understood that structural and logical changes may be made. Sequences of steps are not limited to those set forth herein and may be changed or reordered, with the exception of steps necessarily occurring in a certain order.

Disclosed embodiments provide for collection of images and environmental information from potentially hazardous environments. Disclosed embodiments include a system for obtaining and displaying such images and environmental information from environments, as well as various apparatuses for use in this system. Apparatuses described include a deployable sensor device and a host. Embodiments of the system and the sensor device include a sensor device having an enclosure providing protection from hazardous environmental conditions and shock, the sensor device having camera assemblies and environmental sensors for capturing images and environmental information, respectively, and a communications interface for transmitting these images and environmental information to a host for display and/or analysis. Further, disclosed embodiments include methods for obtaining the images and environmental information.

FIG. 1 shows a system 100 for obtaining environmental information and images, in accordance with embodiments described herein. System 100 includes one or more sensor devices 200 for obtaining environmental information and images, and at least one host 600 for receiving and displaying the environmental information and images from sensor device 200. Sensor device 200 and host 600 interact via a communications link 102. Communications link 102 is preferably a two-way wireless communications interface, such as an 802.11(b) signal, or any other 802.11 wireless communications interface or "Wi-Fi" communications interface, as are commonly known in the art. In another embodiment, communications interface 102 is a wired communications interface, with the connecting interface configured to allow sensor device 200 to be deployed to a desired distance from the host 600.

Figure 2:
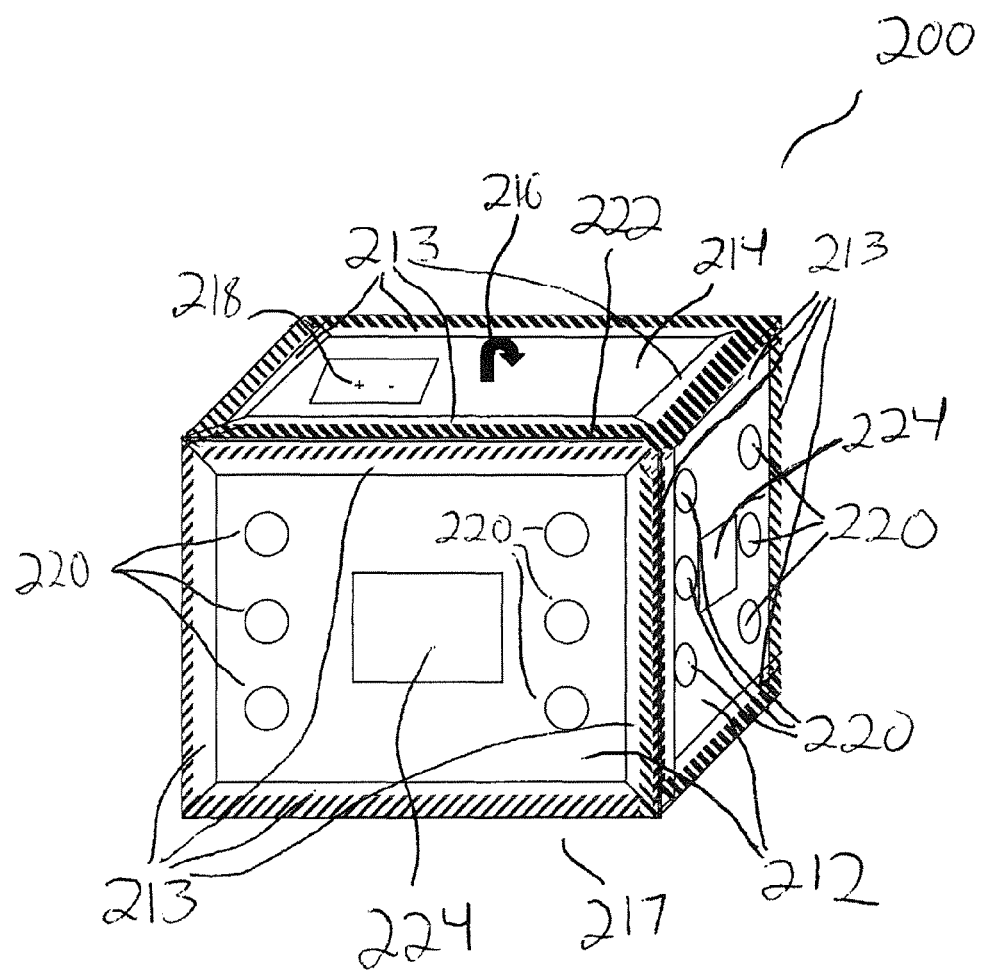
FIG. 2 is a diagram of a sensor device for obtaining environmental information and images, in accordance with embodiments described herein.

FIG. 2 is a diagram of the exterior appearance of sensor device 200, configured to obtain environmental information and images, in accordance with embodiments described herein. In system 100, sensor device 200 is preferably configured to be deployed into an environment by hand. Sensor device 200 therefore should be configured to a size and weight such that a person is capable of moving the device into the environment. For example, a person can deploy sensor device 200 by picking it up and throwing it into the environment. However, the main goal is to promote ease of deployment. Thus, sensor device 200 can be thrown, deployed by remote device (e.g., a robot), dropped out of a vehicle, or through any other means of moving the device into the environment. Sensor device 200 is designed for use in hazardous environments. For example, sensor device 200 is designed to operate in an environment with an ambient temperature in excess of 500 degrees for a substantially longer period of time than other sensor devices.

Sensor device 200 comprises an enclosure 210. In one embodiment, as shown in FIG. 2, enclosure 210 is cubic-shaped, having a top surface 214, a bottom surface 217, and four side surfaces 212. In a further embodiment, enclosure 210 is a cubic-shaped enclosure further comprising rounded or beveled edges 213 surrounding all six faces of sensor device 200. A cubic-shaped enclosure with rounded edges 213 provides for easier deployment of sensor device 200 because the shape allows for sensor device 200 to roll initially while also causing sensor device 200 to stay at rest once its trajectory ceases. Other embodiments of sensor device 200 include alternative shapes for the enclosure 210, such as spherical, hexagonal, or pyramidal shapes.

In a preferred embodiment, a shock-absorbing casing 222 covers edges 213 of the faces of sensor device 200, providing protection to the structural and electrical components of sensor device 200, for instance when sensor device 200 is thrown by hand. Casing 222 is located on the exterior of sensor device 200 and not protected by any insulation, and thus must be capable of withstanding temperatures and/or other environmental elements of hazardous environments. A material that burns, melts, or corrodes under environmental conditions in which sensor device 200 is designed to operate could interfere with operation of camera assemblies 500 and/or environmental sensors 220, potentially disabling sensor device 200 (FIG. 2). A preferred embodiment of casing 222 is made from silicone rubber, such as Silastic™ silicone rubber manufactured by Dow Corning™. Silicone rubber is a flexible yet durable material that is also resistant to extreme temperatures.

Enclosure 210 preferably has dimensions that permit sensor device 200 to be deployed, for example, by hand, and thus preferably has a maximum size that is less than twenty-four (24) inches in length on any one exterior surface, and more preferably, approximately six (6) inches in length on all sides. The minimum size of the enclosure 210 will be determined by the space required to house the electronics assembly 300 and the thickness of the enclosure 210.

In the embodiment of sensor device 200 shown in FIG. 2, sensor device 200 includes side surfaces 212 (two of which are visible in FIG. 2). Side surfaces 212 include environmental sensors 220 and camera portals 224.

Figure 5:
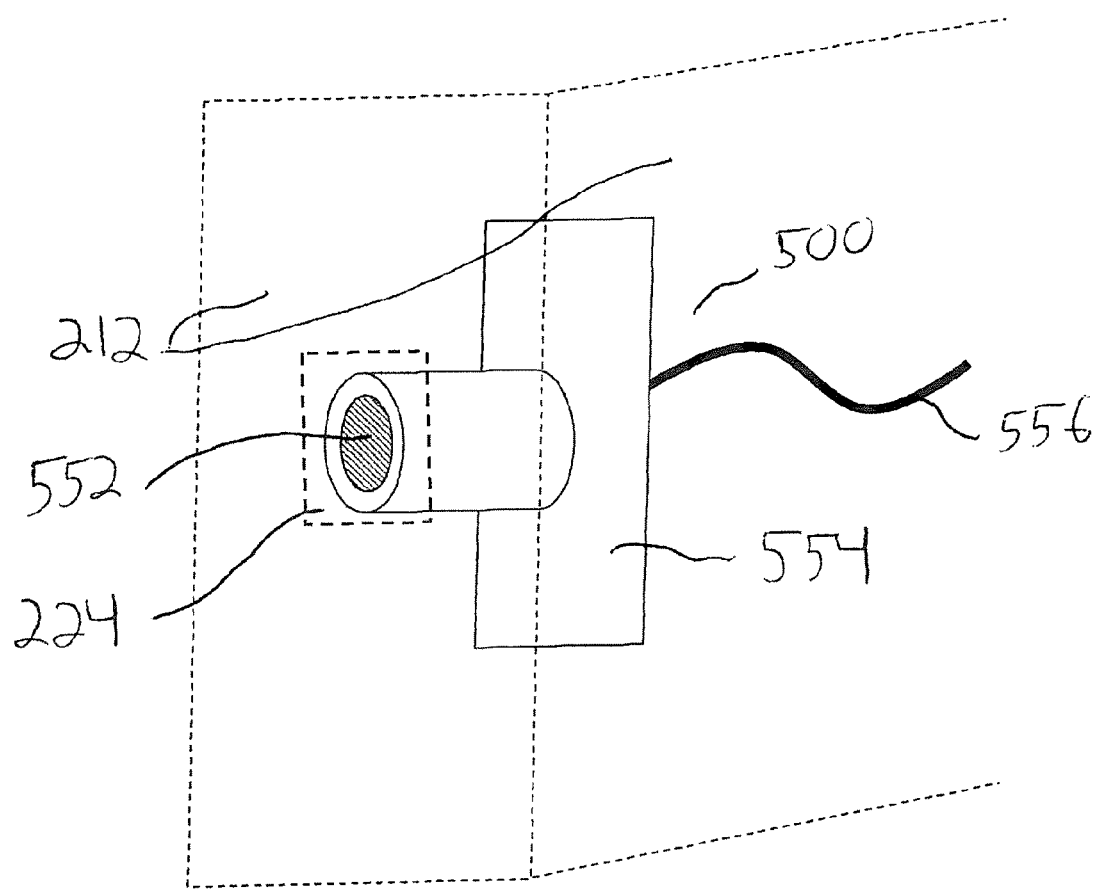
FIG. 5 shows a camera assembly used in a sensor device for obtaining environmental information and images, in accordance with embodiments described herein.

Each camera portal 224 consists of a transparent material affixed in side surface 212 providing for light to pass through the camera portal 224 to a camera assembly 500 (FIG. 5) inlaid within the side surface. Camera portal 212 is a pane of translucent material, such as, for example, quartz crystal glass, or translucent hardened plastics. Alternatively, the camera portal 224 can alternatively be a lens of the camera assembly 500 itself. Each camera portal 224 is flush with the side surface 212 in order to provide better rolling characteristics. Each side surface 212 and camera portal 224 is sealed to prevent water, smoke, and other hazards contained in the external environment from permeating sensor device 200.

Sensor device 200 includes a camera assembly 500 (FIG. 5) inlaid within at least one of its exterior surfaces 212, 213, 214. In the embodiment shown in FIG. 2, each side surface 212 of sensor device 200 has a camera assembly 500 contained within the enclosure 210, with the lens of the camera assembly 500 either located behind and protected by the respective camera portal 224, or comprising the respective camera portal itself.

Figure 3:
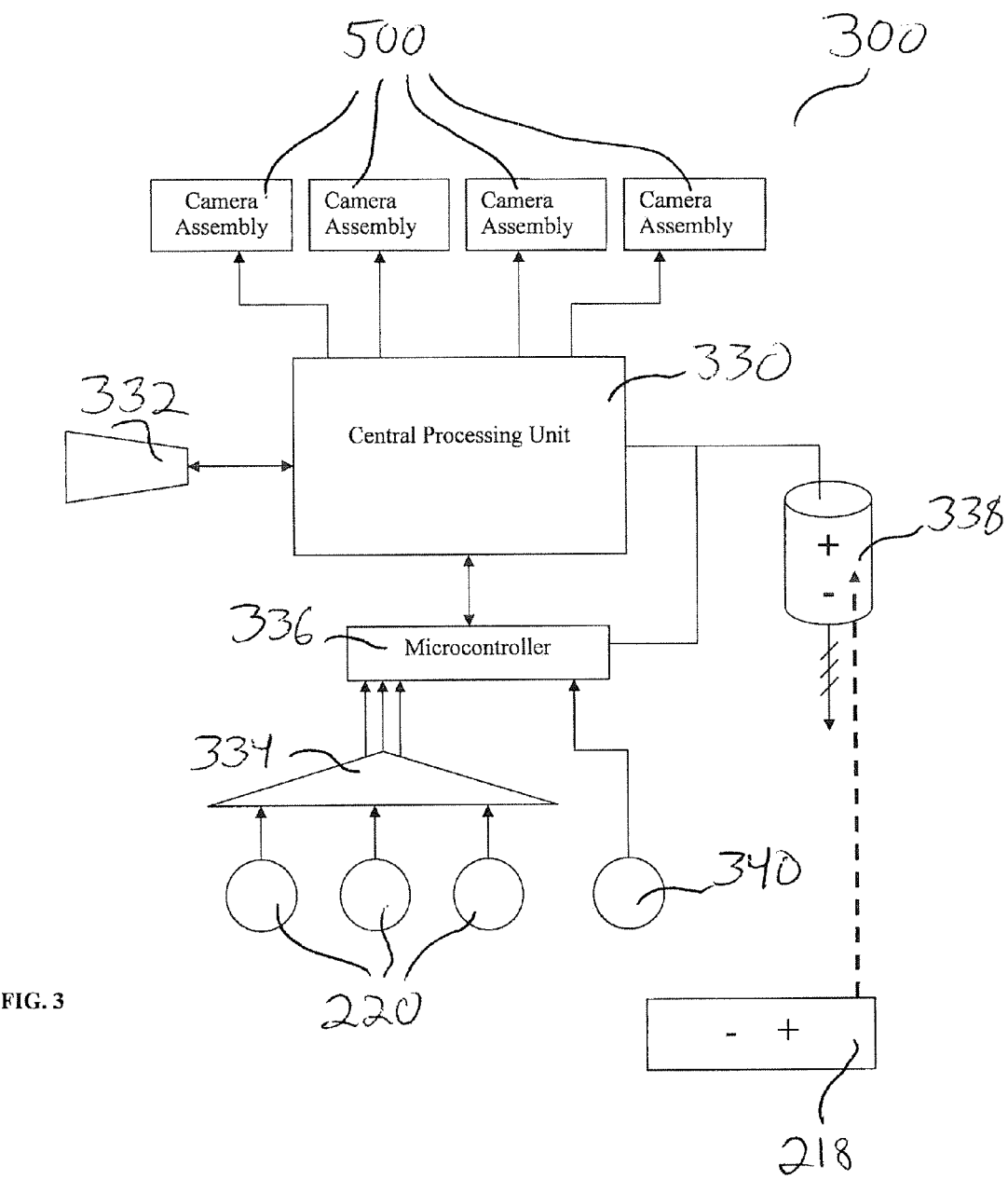
FIG. 3 is a schematic diagram of an electronic assembly of a sensor device for obtaining environmental information and images, in accordance with embodiments described herein.

Camera assembly 500 includes a small board-level camera circuit 554 and camera lens 552. The camera circuit 554 can either consist of a bare circuit board along with a lens mount, thus requiring minimal additional circuitry for each camera assembly 500, or separated sets of components integrated into a single hardened mother board. Camera assembly 500 also includes a camera interface 556 for transmitting obtained images to a central processor 330 (FIG. 3).

Embodiments of camera assembly 500 employ any type of imaging system, including infra-red or other non-visual spectra. Within the visible range, any type of camera technology is used, including CMOS or CCD imaging. While CCD camera assemblies tend to offer better intensity discrimination, CMOS camera assemblies tend to offer faster readout and lower power consumption. Camera assembly 500 is configured to obtain video images, or, alternatively, still images. Camera assembly 500 is configured to obtain color or monochromatic (i.e., black and white) images at any desired resolution that is available. Camera assembly 500 may be selected based upon a variety of factors, including resolution, sensitivity, size, weight, durability, camera interface, and method of exposure control.

In a preferred embodiment, camera assembly 500 includes a monochrome CCD imager system, with a USB interface configured to operate with a Windows™ or Linux™-based processor. Such a camera is provided by Sentech model STC-B33USB. Camera lens 552 has a focal length preferably in the range from 1.7 mm to 3.6 mm, and most preferably 2.5 mm. However, other focal lengths are within the scope of this invention. Camera assembly 500 provides for analog-to-digital conversion of the obtained image signal. Alternatively, camera assembly 500 outputs an analog image signal to central processor 330, and central processor 330 provides analog-to-digital conversion.

Camera assembly 500 is shown inlaid in a side surface 212 of a sensor device, such as sensor device shown in FIG. 2. Camera lens 552 is positioned behind camera portal 224. Camera portal 224 provides a viewpoint for camera assembly 500, while protecting the lens and providing a flush and sealed side surface of sensor device 200 (FIG. 2). In one embodiment, camera lens 552 is perpendicular to the respective side surface 212. In another embodiment, camera lens 552 is located at an angle to the respective side surface 212. For example, camera lens 552 can be directed at an angle slightly above parallel to the ground level, providing greater coverage of the environment.

Referring back to sensor device 200 of FIG. 2, the visible side surfaces 212 of sensor device 200 also include environmental sensors 220. In a preferred version of sensor device 200, environmental sensors for detecting and measuring levels of oxygen, hydrogen sulfide, and carbon monoxide in an environment would be used. It should be understood, however, that sensor device 200 could be configured to detect the presence and/or levels of any environmental condition in which there exists a commercially available environmental sensor. Various environmental sensors are known in the art, and are configured to detect temperature, smoke, or levels of various gaseous elements in the environment. For instance, known environmental sensors include sensors that detect the presence and/or levels of: hydrogen sulfide; oxygen; carbon monoxide; carbon dioxide; chlorine; hydrocarbons; smoke; heat; nuclear and other radiation; poisonous gases and/or particles (e.g., anthrax); and fire suppression agents.

Sensor device 200 also includes a tether attachment connector 216 to enable retrieval of sensor device 200, for example by a mechanical means that connects to the tether attachment connector 216. The tether attachment connector 216 is located on a top surface 214 of sensor device 200 that is designed to face upwards when sensor device 200 is at rest. The tether attachment connector 216, for example, can be a hook, a magnetic or electro-magnetic connection device, or any other connection device designed to allow attachment by a mechanical means, such as a pole or hook. The tether attachment connector 216 is preferably flush with or inlaid in a surface of the enclosure 210 to minimize the effect of the tether attachment connector 216 on the rolling trajectory of sensor device 210.

Sensor device 200 also includes a charging terminal 218 on the exterior of enclosure 210. The charging terminal 218 is used to charge and/or recharge a power source 338 (FIG. 3) of sensor device 200. The charging terminal 218 is preferably located on a top surface 214 of the enclosure 210, as shown in FIG. 2. Alternatively, charging terminal 218 can be located on a side surface 212 or bottom surface 217 of the enclosure 210. The charging terminal 218 is configured to allow serial charging of multiple sensor devices 200 when the sensor devices 200 are stowed; for instance, a charging terminal 218 located on a top and a bottom surface 217 of a sensor device provides for charging of the respective power sources of multiple sensor devices 200 when the multiple sensor devices 200 were stacked on top of one another.

A bottom surface 217 of the enclosure 210 of sensor device 200—that is, a surface intended to rest on the floor when sensor device 200 comes to rest—includes extra weighting, such as a layer or object not included in other surfaces of the enclosure 210. The extra weighting of the bottom surface 217 provides for improved deployment of sensor device 200—when sensor device 200 is thrown or otherwise deployed, it is more likely that none of the side surfaces 212 having camera portals 224 and environmental sensors 220 will be facing the ground and thus incapacitated.

FIG. 3 is a schematic diagram of an electronics assembly 300 of a sensor device 200. Electronics assembly 300 includes the electronic elements of sensor device 300 electronically coupled to a central processor 330. The electronic elements shown in electronics assembly 300 include one or more camera assemblies 500, a power source 338 with an optional charging terminal 218, environmental sensors 220 coupled to an environmental sensor amplifier 334, a board temperature sensor 340, a microcontroller 336 that receives signals from the environmental sensor amplifier 334 and/or the board temperature sensor 340, and a device external communications interface 332. The elements are described further below.

Central processor 330 is configured to provide central control, data acquisition, and communications support for sensor device 200. Central processor 330 receives environmental information from the various environmental sensors 220, images from camera assemblies 500, and supports wireless communications via a device external communication interface 332. The environmental information and images received by the central processor 330 may be either analog or digital, and thus central processor 330 is configured to receive either analog or digital signals, and to provide analog-to-digital conversion of received analog signals. Alternatively, a separate analog-to-digital converter is included in electronics assembly 300 (such as in microcontroller 336). Central processor 330 is also preferably configured to provide compression (i.e., JPEG or MPEG-2 compression) of high-bandwidth digital data, such as still or video images, prior to the transmission of the digital data to host 600 (FIG. 1) via the device external communication interface 332.

Central processor 330 includes a software package configured to acquire and compress images and environmental sensor information, and transmit the images and environmental information over an IP network interface via the external communication interface 332. Any known wireless software package is used. For example, an open-sourced software platform such as Linux™ or any versions of the Windows™ operating system are adaptable to the instant invention. Open-sourced software generally may be freely copied, modified, and used, and thus is conducive to being adapted for use in central processor 330 of sensor device 200.

A preferable software package for central processor 330 includes a camera driver providing operation (i.e., exposure and readout) and control (i.e., exposure conditions such as shutter speed, gain, and clocking rate) of camera assembly 500. Preferably, the software package and camera driver are configured to allow for obtaining and transmitting either still or video images. A preferable software package also includes a module providing for compression of digital signals received by central processor 300. A preferable software package also includes a module for receiving and converting analog signals from environmental sensors 220 and/or board temperature sensor 340, or, alternatively, receiving digitized versions of the environmental information and board temperature information from microcontroller 336 (as further discussed below).

The software package of central processor 330 also preferably includes a module for outputting environmental, image, and/or other data to an external communications interface, i.e., device external communications interface 332. For example, image and environmental data can be output in discrete portions also known as "messages." Each image message contains, for example, one frame of compressed or uncompressed image data from a camera assembly 500. Each environmental message contains, for example, sensor information from all environmental sensors 220 in sensor device 200. Each message is time-stamped for subsequent analysis purposes, and converted into standard TCP/IP or UDP/IP protocols, as is commonly known in the art, for transmission to the host via external communication interface 332.

Electronics assembly 300 also includes one or more environmental sensors 220. As described above, environmental sensors 220 are configured to detect the presence of and/or levels of various gaseous and other environmental conditions, including, but not limited to: hydrogen sulfide; oxygen; carbon monoxide; carbon dioxide; chlorine; hydrocarbons; smoke; heat; nuclear and other radiation; poisonous gases and/or particles (e.g., anthrax); and fire suppression agents.

Environmental sensors 220 are commonly configured to generate an analog signal indicating the presence of and/or a level of an environmental condition. This analog signal generated by environmental sensors 220 typically ranges from less than 0.1 microamps to approximately 100 microamps, depending upon the configuration of the particular environmental sensor 220 and the type and amount of the detected environmental condition in the atmosphere. Electronics assembly 300 also includes an environmental sensor amplifier 334 configured to amplify the analog signals generated by environmental sensors 220. Amplification is often necessary to render the generated analog signals conducive to analog-to-digital conversion. For instance, typical circuits providing analog-to-digital conversion require received analog signals in the range of zero (0) to five (5) volts. Thus, environmental sensor amplifier 334 is configured to provide varying levels of amplification for various environmental sensors, depending upon the amplitude range of the analog signal generated by the respective environmental sensor 220.

The electronic elements in electronics assembly 300 are sensitive to levels of heat and cold. For instance, temperatures in excess of 185 degrees Fahrenheit can render electronic elements inoperative. In addition to ambient heat frequently present in hazardous environments, electronics assembly 300 receives heat generated by the normal operation of electronic elements such as power source 338 and central processor 330. Electronics assembly 300 also includes a board temperature sensor 340 that is configured to monitor the temperature of a portion of the electronics assembly 300, and provide internal temperature information to host 600 (FIG. 1). Board temperature sensor 340 is configured to generate an analog or digital signal indicating the internal temperature of the electronics assembly 300.

Analog signals generated by environmental sensors 220 and/or board temperature sensor 340 are preferably converted to digital signals prior to processing by central processor 330 and transmission via device external communications interface 332. In one embodiment, central processor 330 is configured to provide analog-to-digital conversion of analog signals. In another embodiment, analog-to-digital conversion of analog signals is provided by a microcontroller 338 before the signals are provided to central processor 330. Microcontroller 338 includes analog-to-digital converters configured to sample analog signals from environmental sensors 220 and/or board temperature sensor 340. In this embodiment, microcontroller 338 provides the digitized signals to central processor 330 through a serial interface, such as a RS-232 interface.

Microcontroller 338, for example, includes its own software package configured to provide for acquisition of analog signals from environmental sensors 220 and/or board temperature sensor 340, analog-to-digital conversion of the received analog signals, and transmission of these signals to central controller 330. Such a software package can be written in standard C or C++ programming platform. Alternatively, the software package is adapted for use in sensor device 200 using an open-sourced platform, such as a version of Linux™ for microcontrollers.

Electronics assembly 300 also includes a power source 338 for powering electronic elements including central processor 330 and/or microcontroller 336. Power source 338 also directly powers other elements of electronics assembly 300, such as camera assemblies 500, environmental sensors 220, environmental sensors amplifier 334, board temperature sensor 340, and/or device external communications interface 332. Alternatively, power source 338 powers some or all of these elements of electronics assembly 300 through their respective interfaces with central processor 330 and/or microcontroller 336. For instance, camera assemblies 500 are interfaced to central processor 330 via a serial USB interface that provides a power signal to camera assemblies 500 as well as providing for the transmission of data.

Power source 338 preferably comprises one or more NiMH batteries. NiMH batteries typically have a nominal voltage of 1.2 volts. Depending upon the voltage necessary to power elements of electronics assembly 300, power source 338 may comprise a plurality of NiMH batteries in series. For example, in a preferred embodiment, central processor 330 and microcontroller 336 tolerates a voltage range from approximately 4.7 to 5.3 volts. Thus, four NiMH batteries, each providing a 1.2 volt charge, are linked in series to provide a 4.8 volt charge to central processor 330 and microcontroller 336. In other embodiments, power source 338 may comprise other battery technologies, such as one or more LiON batteries, for example.

Electronics assembly 300 also includes a device external communications interface 332 for transmitting image, environmental, and other information to host 600 via communications link 102 (FIG. 1). External communications interface 332 is preferably configured to transmit digital data via a wireless signal, such as a "Wi-Fi" 802.11 signal, over a range of 100 feet or more. External communications interface 332 is preferably configured to transmit data formatted in standard TCP/IP or UDP/IP protocols. External communications interface 332 preferably provides a two-way communications interface, so that sensor device 200 also receives control and other information from host 600 via communications link 102. Embodiments of external communications interface 332 comprise, for example, a compact flash wireless card with an internal or external antenna. For example, an embodiment of external communications interface 332 comprising a compact flash wireless card by Embedded Works and an antenna (located either external or internal) that provides wireless 802.11 transmission of TCP/IP or UDP/IP data over 400 feet.

Figure 4:
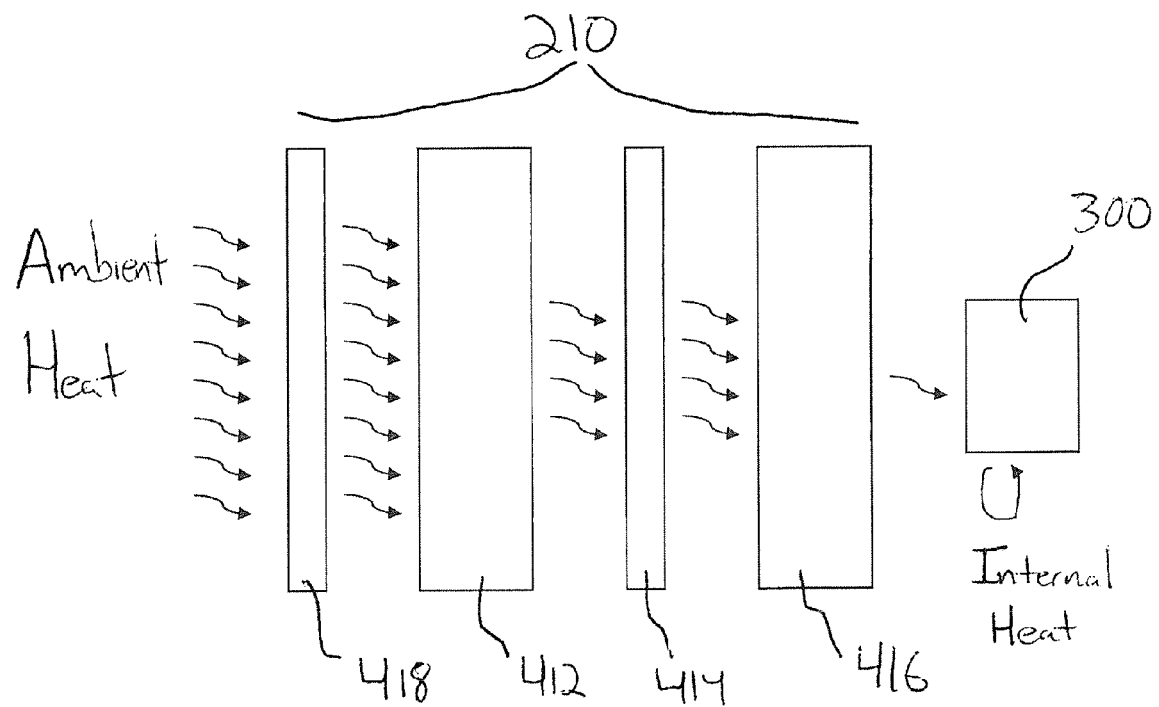
FIG. 4 is a cross-section of a wall of an enclosure of a sensor device for obtaining environmental information and images, in accordance with embodiments described herein.

FIG. 4 is a cross-sectional diagram of a single wall of enclosure 210 of sensor device 200. The wall of enclosure 210 includes an inner structural layer 414 providing the structural integrity of the enclosure 210, an insulating layer 412 for mitigating the effects of environmental heat on electronics assembly 300, and an outer layer 418 for covering and protecting electronics assembly 300 and other components of sensor device 200.

Structural layer 414 is formed from known and readily available formable materials such as, for example, fiberglass, ceramics, engineering plastics, polycarbonate, acrylonitrile butadiene styrene (ABS), or poly-tetrafluoroethene (PTFE or Teflon™). A preferred embodiment of structural layer 414 is formed from fiberglass, because fiberglass is mechanically suited to being deployed into a hazardous environment. For instance, a structural fiberglass layer can be custom formed from known methods, and may be lightweight, resistant to shattering even when damaged, and have low thermal conductivity yet high tolerance to extreme heat and cold.

Insulating layer 412 is designed to be safe for use in temperatures in excess of 500 degrees Fahrenheit. Insulating layer 412 also provides shock absorption protection for the inner structural layer 414 and electronics assembly 300. Insulating layer 412 is formed from known and readily available formable insulating materials such as, for example, silica aerogels, ceramics, thermoplastic polyimides, Nanopore™ thermal insulation, or fiberglass.

A preferred embodiment of insulating layer 412 is formed from a silica aerogel derivative, such as Pyrogel™ manufactured by Aspen Aerogels. Pyrogel™, for example, has a thermal conductivity in the range of 0.0015 W/m-K and 0.0030 W/m-K, depending upon temperature, and has a maximum use temperature of 725 degrees Fahrenheit. Pyrogel™ also provides some shock absorption, and has a flexible base making it less prone to cracking or shattering.

Outer layer 418 provides covering protection to the other layers of enclosure 210 and the components of sensor device 200. Outer layer 418 also includes openings for one or more camera portals 224 or sensors 220 (FIG. 2). Outer layer 418 is not protected by any insulation, and thus must be capable of withstanding temperatures and/or other environmental elements of hazardous environments. A material that burns, melts, or corrodes could interfere with operation of camera assemblies 500 and/or environmental sensors 220, potentially disabling sensor device 200 (FIG. 2). Outer layer 418 also provides some insulation to the other layers and electronics assembly 300.

Outer layer 418 is formed from known and readily available formable materials such as, for example, polyimide film, aluminum foams, fiberglass, or rubbers. In a preferred embodiment, Kapton™ polyimide film is used to form outer layer 418, because of its high tolerance to heat, thin layering, and light weight.

Sensor device 200 also includes a phase change material (PCM) layer 416 to further protect electronics assembly 300 from heat. Phase change materials are materials designed to exploit the fact that a change between phases of matter (solid, liquid, gas) either absorbs or releases energy. PCM's for electronics are designed to change from solid to liquid. By including PCM within enclosure 210, the phase change absorbs energy that would otherwise cause an increase in temperature. The phase change, then, prolongs the amount of time electronics can survive when they are being heated. However, while PCM helps protect against environmental heat, it also acts as an insulator and does not allow the dissipation of heat generated internally by electronics assembly 300. Thus, the use of PCM may reduce run time of sensor device 200 in a room-temperature environment. Therefore, another embodiment of system 100 (FIG. 1) includes multiple sensor devices 200, with some sensor devices 200 that include phase change material 416 for use in high-temperature environments, and other sensor devices 200 that do not include phase change material 416 for non-high-temperature environments (i.e., environments with an ambient temperature less than the maximum operational temperature for electronic elements of sensor device 200).

In one embodiment of a sensor device including PCM, shown in FIG. 4, phase change material 416 is an additional layer of enclosure 210. Alternatively, the interior of enclosure 210 is filled with loose phase change material 416. Loose phase change material 416 is available in microencapsulated or non-microencapsulated form. Microencapsulated PCM comprises numerous microcapsules each having a core that changes phase while suspended within a shell that stays solid. Thus, microencapsulated PCM remains granular, even after multiple use cycles, and will not melt together into a large block, unlike non-microencapsulated PCM. In addition to selecting between microencapsulated or non-microencapsulated PCM, considerations in selecting a suitable PCM for phase change material 416 include the energy required for phase change (usually expressed in terms of kilojoules per kilogram or kJ/kg), and the phase change temperature indicating the temperature at which the PCM changes phase. Microencapsulated PCM material typically provides lower energy absorption than non-microencapsulated PCM.

Preferably, an embodiment of sensor device 200 for use in high-temperature environments includes phase change material 416 requiring a high energy for phase change (usually expressed in terms of kilojoules per kilogram or kJ/kg) and having a phase change temperature slightly lower than the upper temperature limit of electronic elements in electronics assembly 300 (for instance, slightly lower than 185 degrees Fahrenheit for preferred electronic elements). For example, Microtek™ MPCM-52D™ PCM is a microencapsulated PCM with a phase-change energy of approximately 139 kJ/kg and a melting point of approximately 125 degrees Fahrenheit. Other exemplary PCM materials include Honeywell Astor™ Astorphase 54™ PCM, a non-microencapsulated PCM with a phase-change energy of 220 kJ/kg and a melting point of approximately 129 degrees Fahrenheit, and Rubitherm™ RT 54™ PCM, a non-microencapsulated PCM with a phase-change energy of 181 kJ/kg and a melting point of approximately 134 degrees Fahrenheit.

Figure 6A:
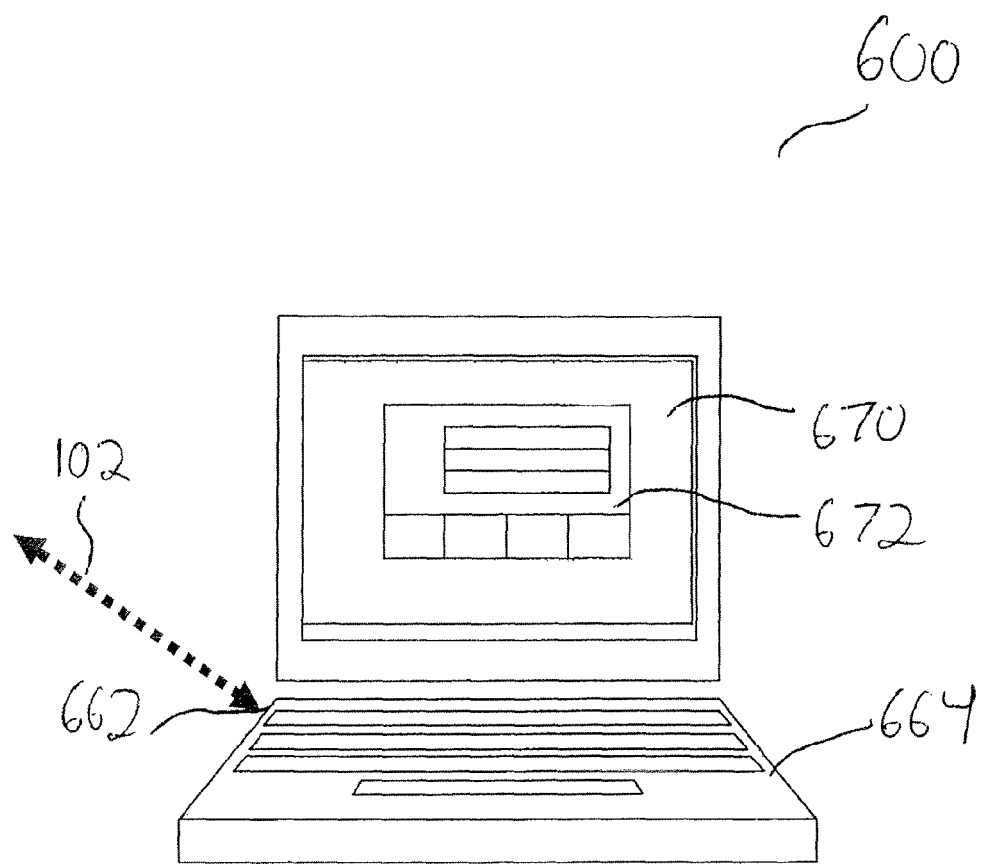
FIG. 6A is a diagram of a host for receiving and displaying environmental information and images obtained by a sensor device, for use with embodiments of a system described herein.

Referring back to FIG. 1, images and environmental information from sensor device 200 is transferred via communications link 202 (for example, a wireless 802.11 "Wi-Fi" communications link) to host 600. FIG. 6A is a diagram of a preferred embodiment of a host for receiving and displaying environmental information and images obtained by a portable sensor device, for use with embodiments of sensor system 100.

In the preferred embodiment, host 600 is a computer system. The computer system can be any known computer system, including, for example, a personal computer such as a laptop computer, a minicomputer, a mainframe computer, a personal digital assistant (PDA), or multiple computers in a system. For example, host 600 comprises a laptop computer with an Intel™ Core Duo™ Processor using x86 architecture. The computer system will typically include at least one display 670, input device 664, and host external communications interface 662, but may include more or fewer of these components. Typically, internal components of host 600 will also include at least one processor, as well as random access memory (RAM). The processor can be directly connected to display 670, or remotely over communication lines such as telephone lines, local area networks, or any other network for data transmission. Host 600 preferably is configured to run on a Linux™ operating system (an open source software platform).

Display 670 of host 600 displays a user interface 672 for presenting all collected images and environmental information collected and transmitted by sensor device 200. In the preferred embodiment, user interface 672 is generated by a Java-based software package, such as a variation of the PanelBuilder™ software package developed by Adaptive Methods™ However, any known or suitable user interface for interaction with cameras and/or sensors can be used.

Figure 6B:
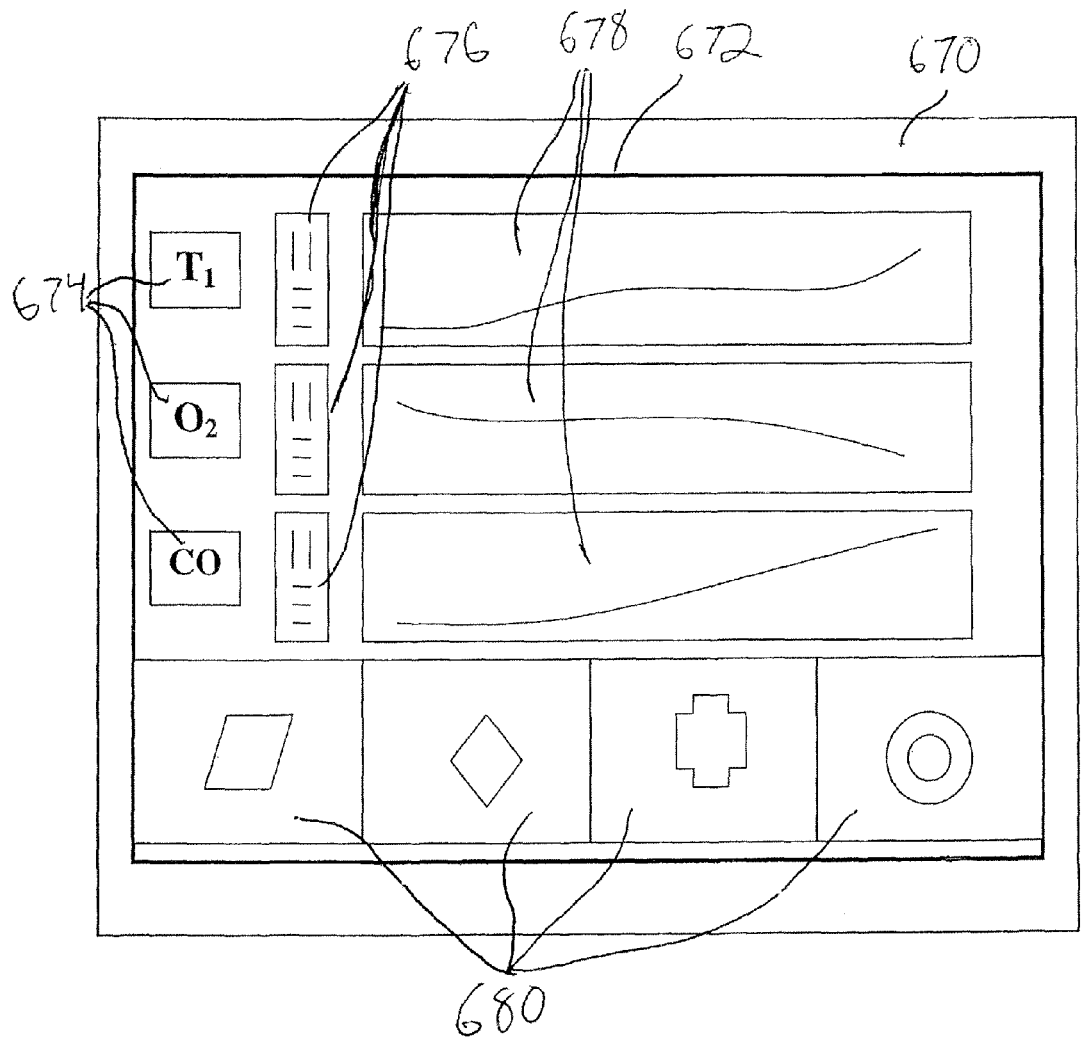
FIG. 6B shows a user interface displaying environmental information and images, for use with embodiments of a system described herein.

FIG. 6B shows an embodiment of user interface 672. In a preferred embodiment of user interface 672 includes an advisory display panel 674, a control display panel 676, an environmental sensor display panel 678, and an image display panel 680.

Advisory display panel 674 displays hardware, software, and/or data advisories related to the operation of sensor device 200 and/or communications link 102 (FIG. 1). These advisories include various color codes and other images associated with various alert levels, categories, and alarms to be presented to the operator. A separate panel provides an operator interface for review of past advisories. Alarms are available for each environmental sensor 220 or environmental condition. If a certain environmental condition is detected (for example a threshold temperature), an alarm is displayed in advisory display panel 674. All such thresholds are XML configurable items and linked to a particular environmental condition detected. An operator of sensor system 100 (FIG. 1) are provided with capability to set thresholds on environmental sensor display panel 678 (discussed below).

Control display panel 676 displays and provides a user interaction with controls for managing information and images displayed on user interface 672. For example, control panel includes a timeline scroll bar for adjusting between the display of current and stored past images and environmental information in user interface 672. Control display panel 676 also displays and provides interaction with controls for controlling sensor device 200 (FIG. 2)

Environmental sensor display panel 678 provides a flexible layout for presenting all collected environmental information from environmental sensors 220. Environmental sensor display panel 678 is dynamically reconfigurable to a single or multi-column format to show all the sensors reporting from the deployed unit. Environmental information is dynamically and automatically added to environmental sensor display panel 678 as it is received. In the event that more environmental information is received than can be reasonably displayed in environmental sensor display panel 678, a vertical scroll bar is provided to scroll amongst environmental information.

Environmental sensor display panel 678 displays separate sub-panels for the environmental information captured by each environmental sensor 220 of sensor device 200 (FIG. 2), or, alternatively, displays separate sub-panels for each environmental condition detected or tested separately. A separate XY chart and/or sensor icon is displayed for each environmental sensor 220 and/or environmental condition displayed. The XY chart displays a time history on the X axis and a level on the Y axis.

Environmental sensor display panel 678 is also configured to adjust characteristics of displayed information according to various thresholds (for example, in accordance with alert levels triggering alerts in advisory display panel 674). The sensor icon and/or XY chart may vary in characteristics such as color, size, or format according to detected environmental conditions. The characteristics are stored so that an operator of sensor system 100 (FIG. 1) can review previous environmental information to see which sensors have exceeded thresholds at anytime in the past.

User interface 672 also includes an image display panel 680 configured to display images obtained by camera assemblies 500 of sensor device 200. Images are dynamically and automatically added to image display panel 680 as they are received. In the event that more images are received than can be reasonably displayed in image display panel 680, a horizontal scroll bar is provided to scroll amongst present and past images. Each individual image panel preferably has control buttons configured to, for example, rotate the individual image clockwise, provide a cursor crosshair, zoom to a cursor crosshair, and/or maximize the individual image to take up the entire display area of user interface 672. Preferably, image display panel 680 is configured to display four images in horizontal panels, each image being the most recent from each of respective four camera assemblies 500 in the previously described preferred embodiment of sensor device 200 (FIG. 2).

Figure 7:
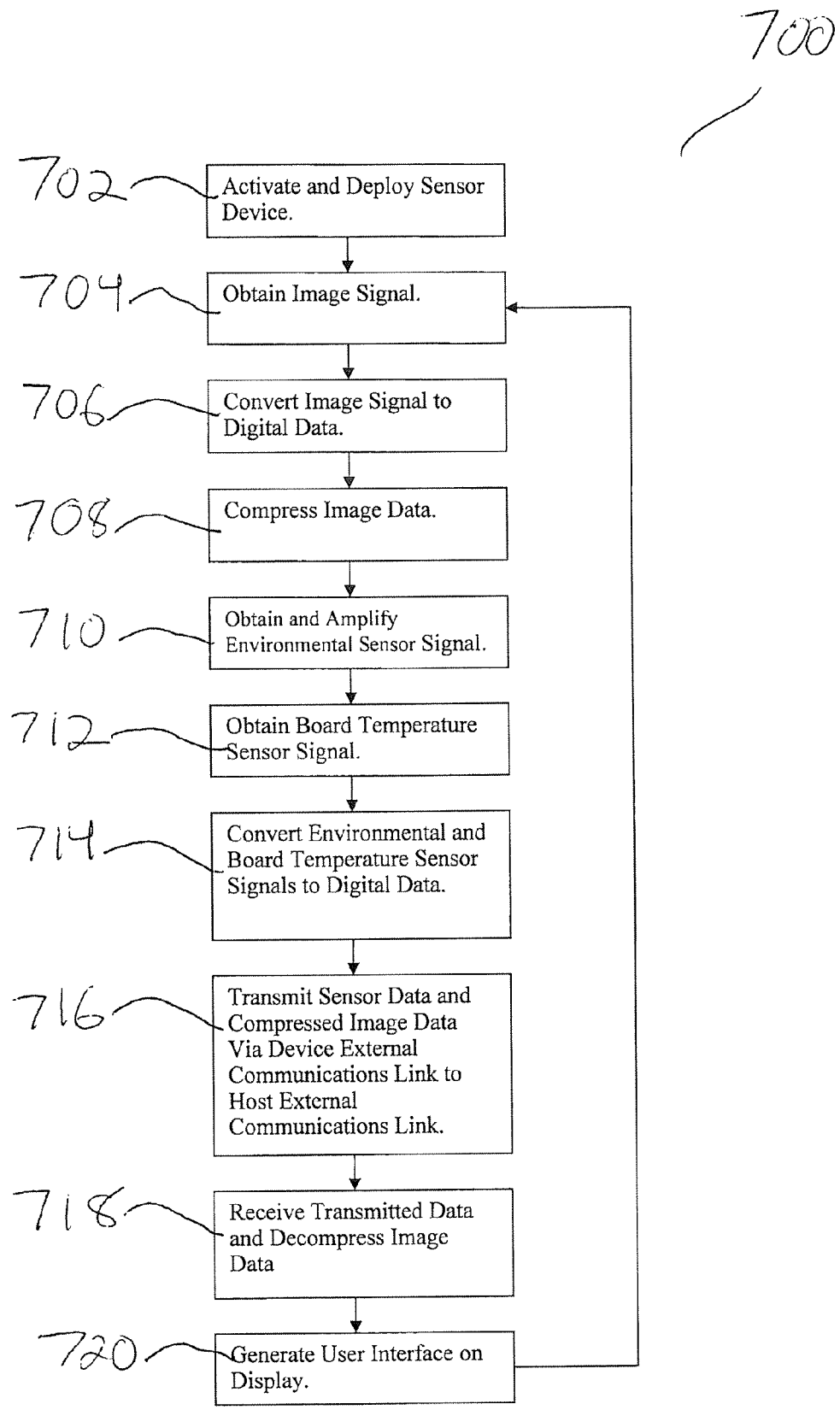
FIG. 7 is a flow chart of a method for obtaining environmental information and images, in accordance with embodiments of a system described herein.

FIG. 7 is a flow chart of a method 700 for obtaining environmental information and images using sensor system 100 described above. In step 702, at least one sensor device 200 is activated and deployed. Sensor device 200 is activated, for example, by a control signal transmitted from host 600 to sensor device 200, by removing a charge from charging terminal 218 (FIG. 2), by activating a switch on sensor device 200, or by any other means of activating an electronic device. Alternatively, sensor device 200 is configured to remain activated during its functional lifetime, or during all times when it may be deployed. In step 702, sensor device 200 is deployed by any known means for deploying a small object. Preferably, sensor device 200 is deployed manually (i.e., by hand) by a person. It should be understood that sensor device 200 may be activated either before or after deployment.

In steps 704-720, sensor system 100 obtains, transmits, and displays images and/or environmental information. It should be understood, however, that steps 704-720 may be conducted continuously, and in any sequence, except when steps necessarily occur in a certain order. Commonly, several steps will be conducted simultaneously. For example, sensor device may obtain images substantially simultaneously while obtaining environmental information, the images and environmental information may be digitized, processed, and/or transferred simultaneously or at different times, and the transmitted images and environmental information may be generated for display on user interface 672 simultaneously or at the different times.

Steps 704-708 relate to obtaining images. In step 704, one or more camera assemblies 500 of sensor device 200 capture images from the environment and convert the images to image signals. In step 706, the analog image signals are converted to digital data through analog-to-digital conversion that is provided by camera assembly 500, or by central processor 330 (FIG. 3). In step 708, the digital image data is compressed to a known compression format (e.g., PEG or MPEG-2), for instance by central processor 330.

Steps 710-714 relate to obtaining environmental information and internal temperature information. In step 710, environmental sensors 220 (FIG. 3) detect the presence of and/or levels of environmental conditions such as temperature and/or hazardous elements in the air. Environmental sensors 220 generate an analog signal according to the presence of and/or level of the particular environmental condition each environmental sensor is configured to detect. In step 712, board temperature sensor 340 optionally detects an internal temperature of sensor device 200 and generates an analog signal according to the detected temperature. In step 714, the analog signals from environmental sensors 220 and/or board temperature sensor 340 are converted to digital data through analog-to-digital conversion that are provided by microcontroller 336 or by central processor 330 (FIG. 3).

In step 716, sensor device 200 transmits the environmental and image data via communications link 102 (FIG. 1) to host 600. Communications link 102 is a two-way communications link provided by device external communication interface 332 (FIG. 3) and host external communications interface 662 (FIG. 6A). Communications link 102 is preferably a wireless communications interface, such as an 802.11(b) signal, or any other 802.11 wireless communications interface or "Wi-Fi" communications interface, as are commonly known in the art. The transmitted data is preferably formatted by central processor 330 to be divided into a series of "messages," each message containing data representing one or more obtained images and/or environmental sensor information. Each message is time stamped for subsequent analysis purposes, and converted into standard TCP/IP or UDP/IP protocols by central processor 330, as is commonly known in the art. The message is then transmitted to host 600 via device external communication interface 332.

In step 718, host 600 receives the transmitted environmental and image data via host external communications interface 662 (FIG. 6A). The received environmental and image data is preferably stored in random-access memory (RAM) by host 600 for immediate presentation purposes. Alternatively, or in addition to being stored in RAM, the received environmental and image data is stored on a hard drive for future analysis and/or presentation. Also in step 718, host 600 decompresses any image or environmental data that was compressed prior to transmission.

In step 720, host 600 generates a user interface 672 on display 670, presenting the received images and/or environmental information from sensor device 200. As discussed above, the most recently received images and environmental information are presented in user interface 672 along with previously received images and environmental information. Preferably, host 600 is configured to present received images and environmental information on user interface 672 automatically and dynamically, as described above.

Embodiments described herein include methods, systems, and apparatuses for obtaining images and environmental information from potentially hazardous environments. The described embodiments provide a system and method for collecting environmental information and images from potentially hazardous environments, while preserving the health and lives of the damage control teams. For example, the embodiments provide for rapid situational assessment of environments such as the compartment of a ship, including views within the compartment and detection of heat and/or other potentially hazardous environmental conditions, thus facilitating coordination of a response and mitigating damage to rescuers, responders, victims, and property.

It should be understood that while preferred embodiments are described, embodiments of the invention are not limited to those described above, but also may include other variants and/or additions. For instance, steps in described methods may occur in varying orders, and several steps may occur in parallel. Components of described apparatuses may include obvious variants and other components that achieve the same functional purpose. Accordingly, the invention should be limited only by the claims below.

The invention claimed is:

1. A portable sensor device for collecting environmental information and images of an environment, the sensor device comprising:
   a cubic enclosure having four substantially flat side surfaces, a top surface, and a bottom surface;
   at least one camera inlaid in at least one of the side surfaces for obtaining the images;
   at least one environmental sensor inlaid in at least one of the side surfaces for obtaining the environmental information; and
   a communications interface for transmitting the images and the environmental information from the sensor device to a remote device.

2. The portable sensor device of claim 1, wherein the external communications interface is a wireless communications interface for transmitting a wireless signal to the remote device.

3. The portable sensor device of claim 1, wherein the multi-faceted enclosure is water-sealed.

4. The portable sensor device of claim 1, further comprising a casing covering edges of the multi-faceted enclosure that provides shock absorption.

5. The portable sensor device of claim 1, wherein the enclosure further comprises rounded edges or beveled edges surrounding each of the surfaces.

6. The portable sensor device of claim 1, further comprising:
   camera assemblies inlaid in each of the four side surfaces; and
   environmental sensors inlaid in each of the four side surfaces.

7. The portable sensor device of claim 6 further comprising:
   a tether attachment connector located on the top surface for retrieving the sensor device.

8. The portable sensor device of claim 6 further comprising:
   a charging terminal located on at least one of the top, side, and bottom surfaces for providing a charge connection to a power source of the sensor device.

9. The portable sensor of claim 1, the bottom surface further comprising a weighted material for making the bottom surface heavier than the side and top surfaces.

10. The portable sensor of claim 1, further comprising:
    a casing lining edges of the cubic enclosure for providing shock absorption.

11. The portable sensor of claim 1 further comprising:
    a camera portal in the at least one side surface including a camera, wherein the camera portal protects a lens of the at least one camera in the at least one side surface.

12. The portable sensor of claim 1, wherein the at least one camera is configured to obtain still images over successive periods.

13. The portable sensor of claim 12, wherein the periods have a duration less than two seconds.

14. The portable sensor of claim 1, wherein the at least one camera is configured to obtain video images.

15. The portable sensor of claim 1, wherein the environmental sensors are configured to obtain a temperature of the environment.

16. The portable sensor of claim 1, wherein the environmental sensors are configured to obtain at least one of:
    levels of hydrogen sulfide in the environment;
    levels of oxygen in the environment; and
    levels of carbon monoxide in the environment.

17. The portable sensor of claim 1, wherein the environmental sensors are configured to obtain at least one of:
    levels of carbon dioxide in the environment;
    levels of chlorine gas in the environment;
    levels of hydrocarbons in the environment;
    levels of smoke in the environment;
    levels of fire suppression agents in the environment;
    levels of radiation in the environment.

18. The portable sensor of claim 1, further comprising an electronics assembly including:
    at least one central processor for receiving image data generated by the at least one camera and environmental information generated by the at least one sensor, and for outputting the received data to the external communications interface; and
    a power source for providing power to the at least one central processor.

19. The portable sensor of claim 18, wherein the environmental sensors generate analog environmental information, the electronics assembly further comprising:
    an amplifier for amplifying the analog environmental information generated by the environmental sensors; and
    a microcontroller for receiving and converting the amplified analog environmental information to digital environmental information, the microcontroller outputting the digital environmental information to the central processor.

20. The portable sensor of claim 18, wherein the power source receives a charge from a charging terminal located on one of the top, bottom, or side surfaces.

21. The portable sensor of claim 1, wherein the sensor device is configured to function in environments with temperatures in excess of 500 degrees Fahrenheit.

22. The portable sensor of claim 1, the side surfaces of the enclosure further comprising:
    a first layer consisting of a shock absorbing material;
    a second layer consisting of an insulating material; and
    a third layer consisting of a structural material for forming the structure of the enclosure.

23. The portable sensor of claim 22, wherein:
    the shock absorbing material is a silicone rubber;
    the insulating material is a silica aerogel derivative; and
    the structural material is fiberglass.

24. The portable sensor of claim 22, further comprising:
a phase change material located near the electronics assembly configured to absorb energy from heat.

25. The portable sensor of claim 1, wherein a lens of the at least one camera is flush with the respective at least one surface.

26. The portable sensor of claim 1, wherein a lens of the at least one camera is protected by a portal, the portal being flush with the respective at least one surface.

27. The portable sensor of claim 1, wherein the external communications interface is configured to transmit the images and environmental information to a computer.

28. A system for collecting images and environmental information, the system comprising:
a host comprising:
a display for viewing a user interface configured to display the environmental information and images;
a user input device configured to provide user interaction with the user interface; and
a host external communications interface for receiving data from an external source;
a portable sensor device configured to obtain and provide the environmental information and images, the portable sensor device comprising:
a device external communications interface for transmitting the environmental information and images to the host;
a cubic enclosure having four substantially flat side surfaces, a top surface, and a bottom surface;
at least one camera inlaid in at least one of the side surfaces for obtaining the images; and
at least one environmental sensor inlaid in at least one of the side surfaces for obtaining the environmental information.

29. The system of claim 28, wherein the host external communications interface and the device external communications interface transmit and receive data via a wireless communications link.

30. The system of claim 29, the sensor device further comprising:
camera assemblies inlaid in each of the four side surfaces; and
environmental sensors inlaid in each of the four side surfaces.

31. The system of claim 28, wherein the sensor is configured to obtain images and environmental information in hazardous environmental conditions.

32. The system of claim 31, wherein the sensor is configured to withstand hazardous environmental conditions including heat in excess of 500 degrees Fahrenheit.

33. The system of claim 29, wherein the user interface is configured to display:
the images obtained by the sensor device;
the environmental information obtained by the sensor device;
controls for user interaction with the sensor device; and
advisory information containing indications generated by the user interface based upon the environmental information.

34. A method of collecting images and environmental information, the method comprising:
deploying a handheld portable sensor device by throwing the portable sensor device into a hazardous environment, wherein the handheld portable sensor device comprises a cubic enclosure having four substantially flat side surfaces, a top surface, and a bottom surface;
obtaining images with the sensor device;
obtaining environmental information with the sensor device;
transmitting images and environmental information from the portable sensor device to a host.

35. The method of claim 34, wherein the portable sensor device comprises:
at least one camera inlaid in at least one of the side surfaces for obtaining the images; and
at least one environmental sensor inlaid in at least one of the side surfaces for obtaining the environmental information.

36. The method of claim 35, the sensor device further comprising:
camera assemblies inlaid in each of the four side surfaces; and
environmental sensors inlaid in each of the four side surfaces.

37. The method of claim 34, further comprising:
monitoring the temperature of electronic equipment contained in the sensor device.

38. The method of claim 34, wherein the hazardous environment includes heat in excess of 500 degrees Fahrenheit.

39. The method of claim 34, wherein the environmental information obtained includes temperature of the hazardous environment.

40. The method of claim 34, wherein the environmental information obtained includes at least one of:
levels of carbon monoxide in the environment;
levels of oxygen in the environment; and
levels of hydrogen sulfide in the environment.

41. The method of claim 34, wherein the environmental information obtained includes at least one of:
levels of carbon dioxide in the environment;
levels of chlorine gas in the environment;
levels of hydrocarbons in the environment;
levels of smoke in the environment;
levels of fire suppression agents in the environment;
levels of radiation in the environment.

42. The method of claim 34, wherein the hazardous environment is a compartment of a ship.

43. The system of claim 28, the bottom surface of the portable sensor device further comprising a weighted material for making the bottom surface heavier than the side and top surfaces.

44. The method of claim 35, wherein the bottom surface of the portable sensor devices comprises a weighted material for making the bottom surface heavier than the side and top surfaces.

45. The method of claim 35, wherein the portable sensor device further comprises a communications interface for transmitting the environmental information and images to the host.

* * * * *